United States Patent [19]
Axelrod

[11] Patent Number: 5,444,535
[45] Date of Patent: Aug. 22, 1995

[54] HIGH SIGNAL-TO-NOISE OPTICAL APPARATUS AND METHOD FOR GLASS BOTTLE THREAD DAMAGE DETECTION

[75] Inventor: Norman N. Axelrod, New York, N.Y.

[73] Assignee: Labatt Brewing Company Limited, London, Canada

[21] Appl. No.: 103,652

[22] Filed: Aug. 9, 1993

[51] Int. Cl.$^6$ .................................................. G01J 4/00
[52] U.S. Cl. ...................................... 356/369; 356/240; 356/446; 250/223 B
[58] Field of Search ................ 356/364, 365, 366, 367, 356/369, 239, 240, 428, 445, 446; 250/223 B; 348/127

[56] References Cited

U.S. PATENT DOCUMENTS

| | | | |
|---|---|---|---|
| 3,653,767 | 4/1972 | Liskowitz | 356/366 |
| 4,459,023 | 7/1984 | Reich et al. | 356/240 |
| 4,902,137 | 2/1990 | Krieg et al. | 356/240 |

Primary Examiner—Richard A. Rosenberger
Assistant Examiner—Robert Kim
Attorney, Agent, or Firm—Morgan & Finnegan

[57] ABSTRACT

An optical photodetection apparatus for glass surface defect photodetection includes a source for directing light, as an incident beam thereof against a glass surface target, which source is selected to emit light at wavelengths substantially overlapping a target-glass-absorbed bandwidth. The apparatus further includes a first optical polarizer for polarizing light emitted from the source, such that the first optical polarizer passes a resultant, polarized, incident beam against a target glass surface. The detector comprises an at least one silicon photodetector, and further includes a second optical polarizer arranged in cross-polarized relation to the first optical polarizer. The detector is aligned in defect scattered light beam detecting relation relative to the incident beam, preferably at an angle in the Brewster range, and is operable to generate a detected signal in response to light scattered through defects in said target surface.

32 Claims, 15 Drawing Sheets

REFLECTANCE VERSUS INCIDENT ANGLE

HIGH SIGNAL-TO-NOISE OPTICAL APPARATUS AND METHOD FOR GLASS BOTTLE THREAD DAMAGE DETECTION

FIELD OF THE INVENTION

The present invention relates to a high signal to noise ratio optical detection apparatus and a method for defect photodetection applications (especially surface defects in glass and in particular in threaded glass bottle necks) requiring high levels of sensitivity and specificity in optical discrimination for predetermining defect responsive threshold conditions. More specifically, this relates to a system capable of distinguishing between defects of various sizes, and for detecting defects in glass bottle threads while avoiding "false positive" defect signals.

BACKGROUND OF THE INVENTION

Defect detection on glass-ware surfaces, particularly along crimped-crown-engaging surfaces is inherently problematic in high volume production applications. Detection is an essential quality assurance issue, since consumers view glass breakage as a material safety concern. Accordingly, it is important to reliably screen out all flawed bottles.

The high volume unit throughput adds to the difficulty of examining each and every bottle, and automated systems are essential for coping with the large numbers of bottles that have to be checked.

Moreover, even in automated systems, the setting of any kind of reasonably conservative detection thresholds with a view to identifying and screening out the preponderance of potential bottle failures seems to invariably lead to unacceptably high collateral rates of unnecessary rejection—that is bottles are identified as false positives for indicia of incipient breakage, when in fact they are not part of the "at risk" target group.

Discrimination between acceptable and unacceptable bottles is a two part process. The first step entails discriminatory sensing, and the second step entails discriminatory processing. Of the two, it is important to note that the efficacy and flexibility of the processing is contingent on the data quality that can be drawn from the sensing step.

The reliability of optical sensing for this purpose is frustrated by both external and internal reflections at bottle surfaces. This coupled with the fact that bottle surfaces are rarely flat, and may even be threaded or otherwise embossed, greatly exacerbates the problem of "noise" in defect "signal" acquisition. The "signal" must be sensitive enough to convey the qualitative and quantitative information necessary to discriminate surface damage from bottle threads.

Moreover, while highly sensitive optical sensing may be useful in applications for relatively pristine, single-trip, bottles onto which thin gauge crowns are rolled formed in-situ (as is common practice in the North American soft drink market, for example), the same may not be applicable to bottles which make multiple return trips, particularly where, as in the beer industry, the crowns are heavy gauge material that is crimped on under much more rigorous conditions than are ever employed in the aforementioned case. In the latter case, quantitative information relating the degree of damage is essential to effective discrimination.

Optical sensing systems are therefor broadly useful only to the extent that they can provide an information-rich signal that is readily and reliably discernable over any incidentally acquired noise, so that both the qualitative and quantitative aspects of that information are made available for use in the subsequent processing step. Accordingly a high "signal to noise" ratio is required if optical sensing is to be employed successfully in appropriately discriminating between bottles having damage that renders them prone to breakage, from those that are either not damaged or whose current-state of imperfection is not likely to engender bottle failure during at least the next succeeding trip.

One approach to optical sensing relies upon the use of a camera coupled with a computer. The camera is adapted to capture an image including details of the bottle thread, which it then passes to the computer. The computer matches the camera image with an overlapping "ideal" image that was previously stored in the computer, and then reacts to variations between the two images. This approach requires that the two images be mapped in a thread-matched overlay registration. Since the bottles in a high-speed, screening queue arrive at the camera viewing station with the threads presented in a random orientation, the computer must expend substantial computing resources to provide for the necessary image registration matching, even before it can effect the discriminatory processing step. This requires processing time and, as a practical matter, also requires substantial capital investment in raw computing power if the system is to cope with the large unit throughput of bottles that is encountered in contemporary industrial settings.

Accordingly, there remains a need in the art for high speed optical sensing that makes high signal-to-noise ratio information available for subsequent processing.

SUMMARY OF THE INVENTION

In accordance with the practice under one aspect of the present invention, there is provided an optical detection apparatus for use in glass surface defect photodetection. The apparatus in question comprises a source for emitting light and is arranged to pass same to a first optical polarizer for polarizing light emitted from the source. The resultant, polarized, incident beam is then incident on a target glass surface.

The detector employed in this apparatus comprises at least one light-source compatible photodetector, (and preferably a camera comprising an array of photodetectors), coupled with a second optical polarizer which is arranged in cross-polarized relation to the first optical polarizer. The detector is arranged in target-surface, defect-scattered-light-receiving relation, relative to the light source. The duly arranged detector is operable to generate a detected signal in response to photons reflected from the target surface. The detector is preferably aligned at about the Brewster angle. The detector preferably comprises a camera linked in tandem to an analog-to-digital detected signal converter operable to provide a digital output signal embodying data representative of the image captured within the camera's field of view. (This is a preferred embodiment—the invention could of course be practised using analog detection alone, if desired).

That data preferably includes a representative array comprising a plurality of reflected-beam-descriptive values for respective values of a corresponding array of camera-sensed pixels. Each of those values represents a relative intensity of the reflected beam as captured within a corresponding one of the pixels.

Preferably the apparatus also comprises a comparator means for establishing defect threshold intensity limits and for comparing the values to the above mentioned limits to identify a defect condition, whereupon the comparator generates a defect-condition responsive output signal. A simple electronic threshold filter may be employed for this purpose. Alternatively, the comparator can employ a discriminatory paradigm, in known manner, selected from the group consisting of: an electronic threshold filter; a deterministic arithmetic thresholding processor; an expert data base coupled with an inferential engine processor; an auto-associative neural network processor; or, any combination thereof, for comparing the limits to the values and triggering the comparator to generate the defect-condition responsive output signal.

The detector optionally further includes a filter, such as an infra-red-rejecting filter, for example, if same is needed to reject light at wave lengths below (or above) a selected polarizer's range of effective polarization.

The forgoing provides for relatively improved signal to noise ratios through cross-polarization in the defect detecting reflected signal. The two, mutually optically offset (ie "crossed") polarizers are arranged in respective incident light polarizing and reflected light receiving relation. These, in combination with the photodetector(s) operate to improve the signal to noise ratio by reducing external surface reflection noise from the glass surface. This enhances the rejection rate of reflected noise without undue collateral defect-signal attenuation.

In accordance with another aspect of the present invention there is provided an optical detection apparatus for use in glass surface defect photodetection, comprising:

means for directing light at wavelengths substantially overlapping a target-glass-absorbed bandwidth, and arranged to pass an incident beam thereof against a target glass surface;

a detector comprising an at least one photodetector, with the detector arranged in defect-scattered beam detecting relation relative to the incident beam and being operable to generate a detected signal in response to defect-transmitted light from defects on the target surface.

In this aspect of the present invention, the means for directing light preferably comprises a source for emitting light, and an optical transmission filter means selected to transmit incident light at wavelengths substantially overlapping a target-glass-absorbed bandwidth, and arranged to pass a resultant, filtered incident beam against a target glass surface. This achieves an internal-reflectance noise suppression through absorption attenuation of internally reflected light.

The filter preferably comprises narrow band pass filter. For example, in one form, the narrow band pass filter means comprises a co-operable pair of narrow band pass filters arranged in optical tandem, and having an overlapping range of transmission bandwidths over a low transmittance range of target glass absorbed wavelengths. Note that absorbence attenuation through the use of a narrow band optical filter that yields an incident beam at wavelengths having essentially 0% transmittance in the target glass, are not preferred. Although attenuation of internal reflectance noise is maximized under such conditions, there is also a collateral signal attenuation at some detection angles—(it appears that at least some light penetration into the glass actually promotes the detection of some defects from some angles). Complete absorption of the incident wavelengths by the target glass defeats this end, and therefore is less desirable than filters which pass some minor proportion of glass-transmissible wavelengths.

Accordingly, it is preferred that the filter be selected such that the incident light transmitted by said filter has a transmittance in said target glass of greater than 0%, and less than 10%, (preferably about 4%).

While narrow band pass filters can be used, it is preferred that the filter comprise a short-pass filter means selected to pass wavelengths in a transmission bandwidth over a low transmittance range of target glass absorbed wavelengths, (bearing in mind the factors mentioned in the last preceding paragraph).

DETAILED DESCRIPTION OF A PREFERRED EMBODIMENT

Introduction to the Drawings

Figure 8:
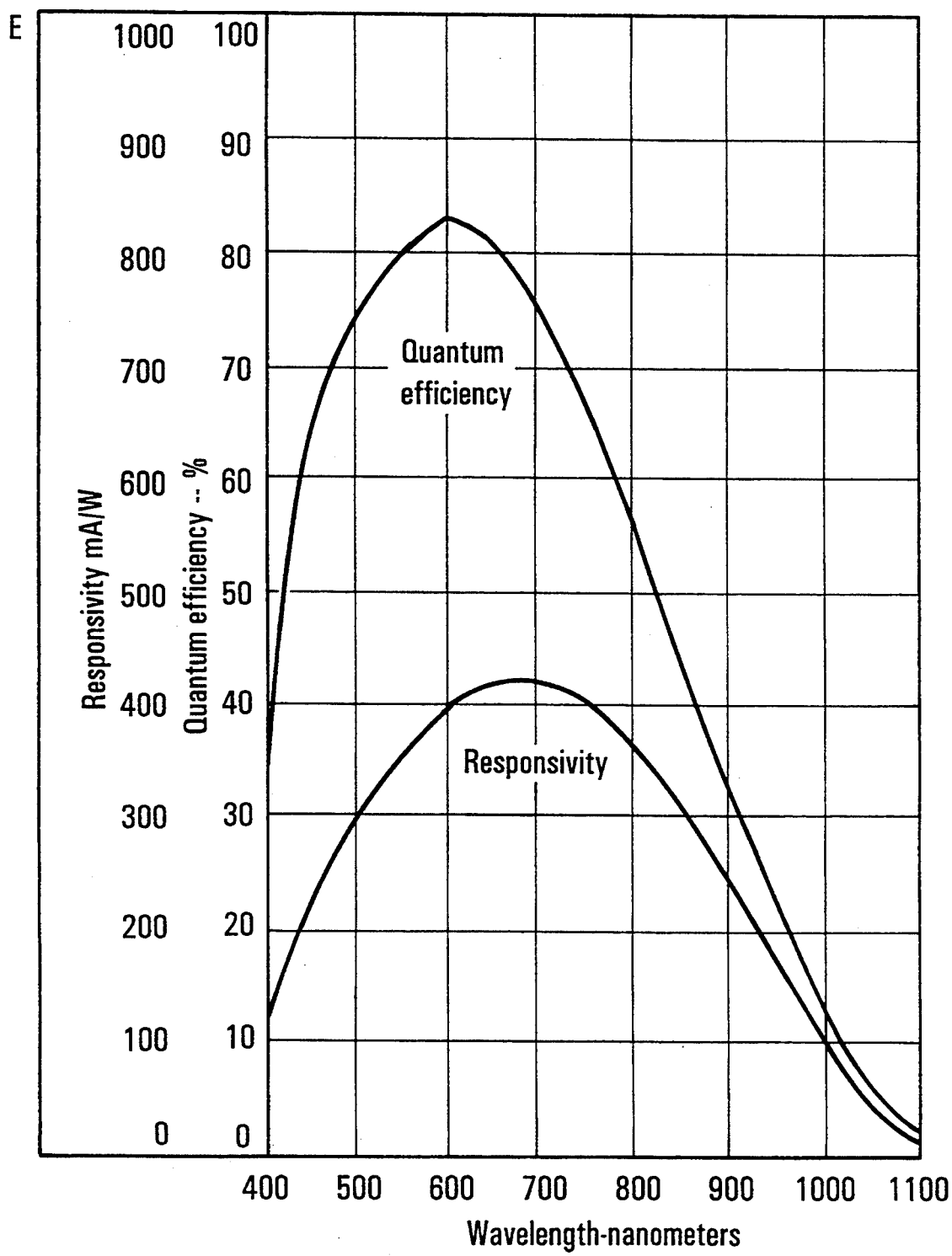
Figure 9:
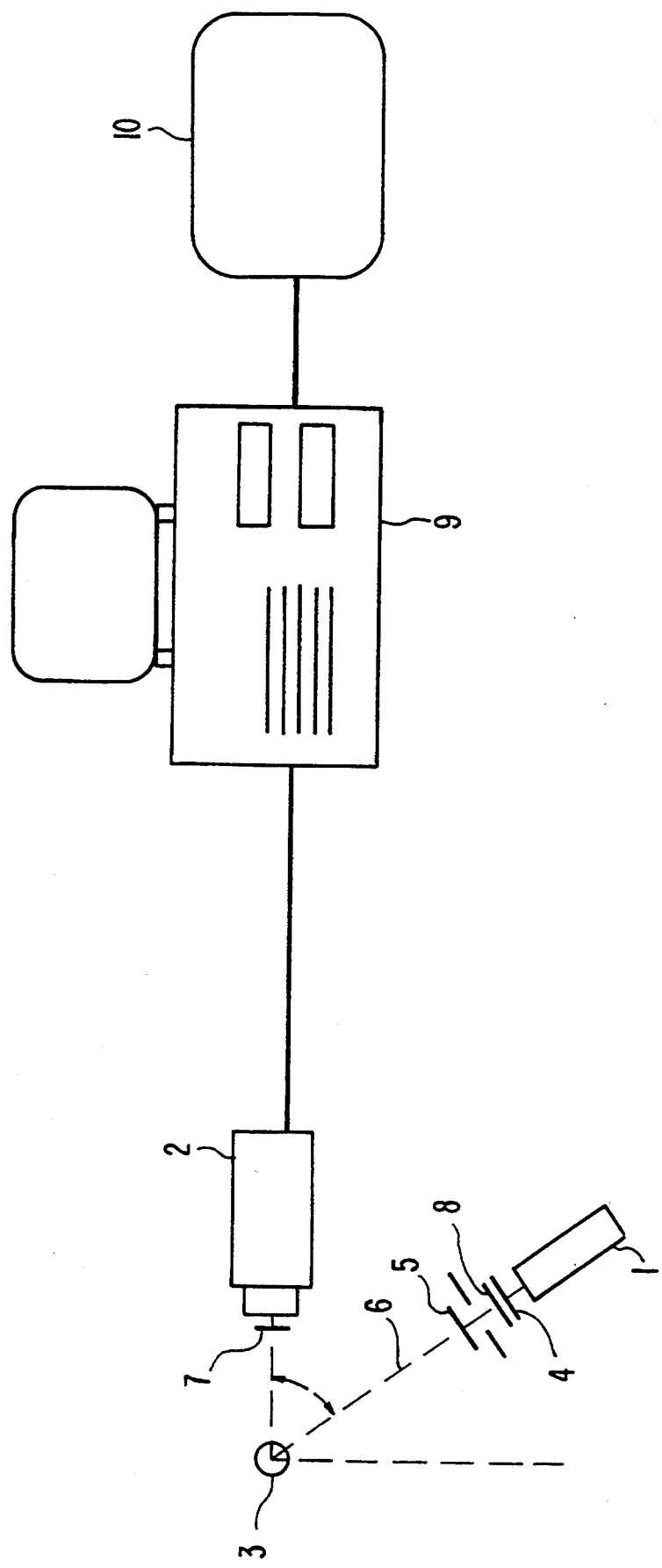
Figure 10:
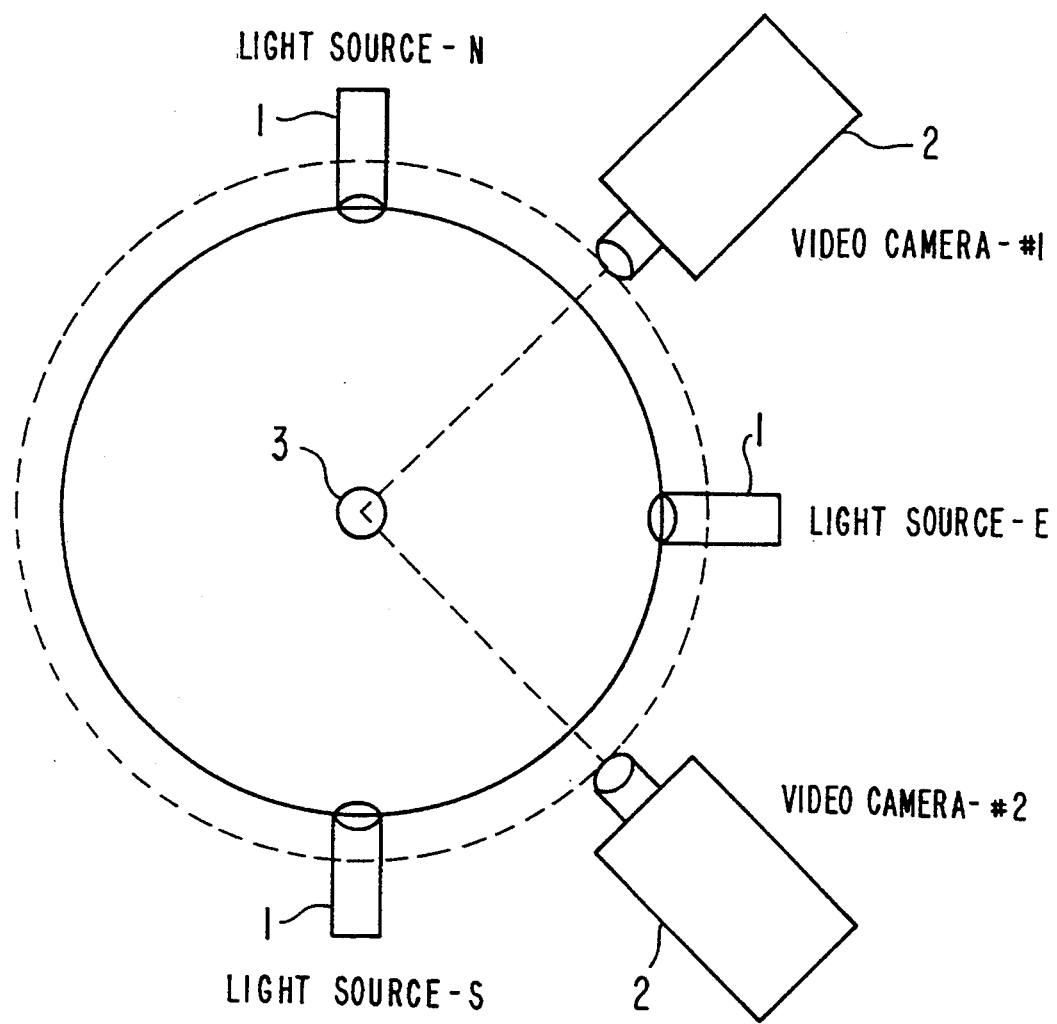
Figure 11:
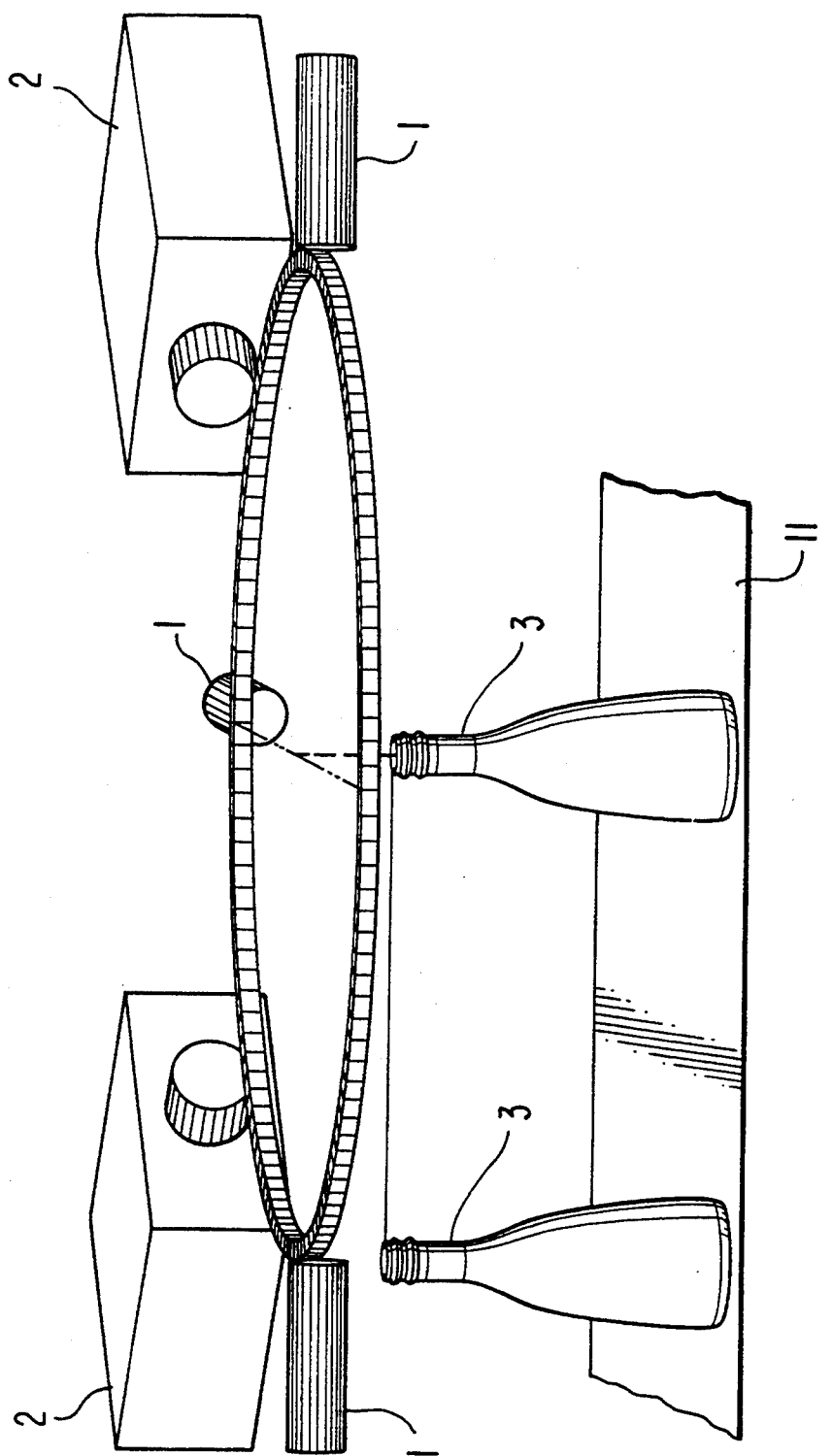

FIG. 8 graphically depicts the spectral response profile of a silicon photodetector COD sensor (model SID 504) from RCA;

FIG. 9 is a stylized representation of a photodetector apparatus according to the present invention;

FIG. 10 is a plan view of a multiple light source, multiple detector arrangement of a photodetector apparatus according to the present invention; and, FIG. 11 is an elevated side view perspective of the apparatus illustrated in FIG. 10.

In accordance with the preferred practice under the present invention, there is provided an optical photodetection apparatus for use in glass surface defect photodetection including: means for directing light as an incident beam thereof against a target glass surface; and, a detector operable to generate a detected signal in response to light scattered (eg scattered and/or transmitted) from the target surface.

Light having wavelengths of less than about 6000 Angstroms, down to an including ultraviolet wavelengths is preferred. Preferably the light source primarily emits in the range of about 4000 to 6000 or 5600 Angstroms, with wavelengths of about 4000 to 5500 Angstroms being especially preferred.

In particular, the preferred practice in accordance with the present invention relates to improvement in defect-detecting, reflected signal-to-noise ratio in a photodetection apparatus in which:

1) the means for directing light is selected to emit light at wavelengths overlapping a target-glass-absorbed bandwidth, and
2) the photodetector apparatus further includes a first optical polarizer for polarizing light emitted from the means for directing light, wherein the first optical polarizer is arranged to pass a resultant, polarized, incident beam against a target glass surface; and,
3) the detector comprises at least one photodetector further including a second optical polarizer arranged in cross-polarized relation to the first optical polarizer, and wherein the detector is aligned in reflected beam detecting relation relative to the incident beam, at about the Brewster angle, and is operable to generate a detected signal in response to light scattered from defects in the target surface.

The means for directing photons preferably comprises a filtered tungsten-halogen light source, coupled through an incident-beam-directing fibre optic pipe, to a lens that aids in focusing the incident beam over a target surface area.

Preferably, the surface illumination pattern covers a rectangular target field. This can be accomplished by masking the emitting end of the optical fibre, or utilizing a rectangular-shaped aperture. An optical fibre having a rectangular cross-section is, however, the preferred approach.

Figure 1:
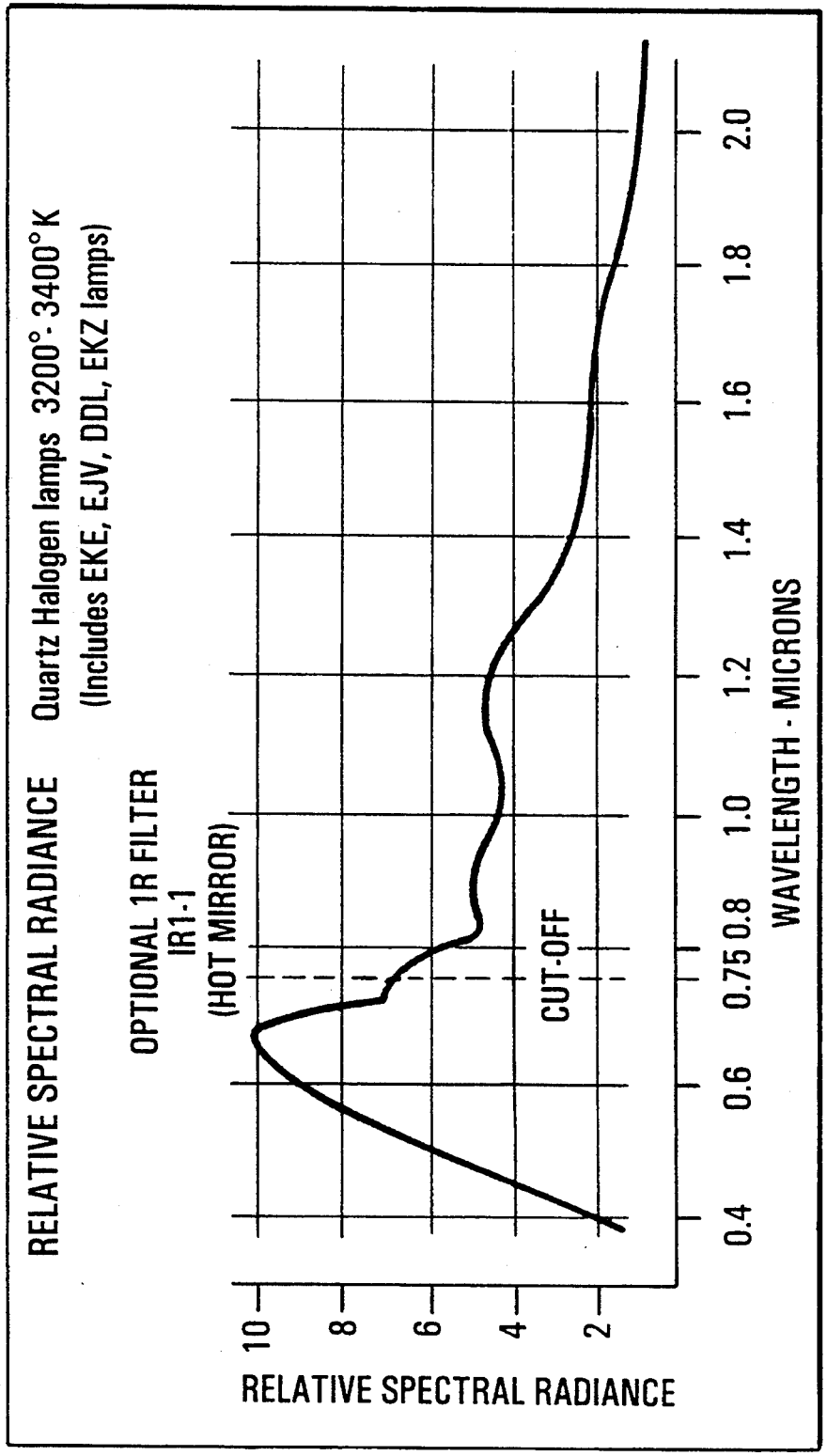
FIG. 1 is a graphical depiction of the relative spectral radiance output of a tungsten quartz halogen lamp used as a photon source in the practice of the present invention.
Figure 2:
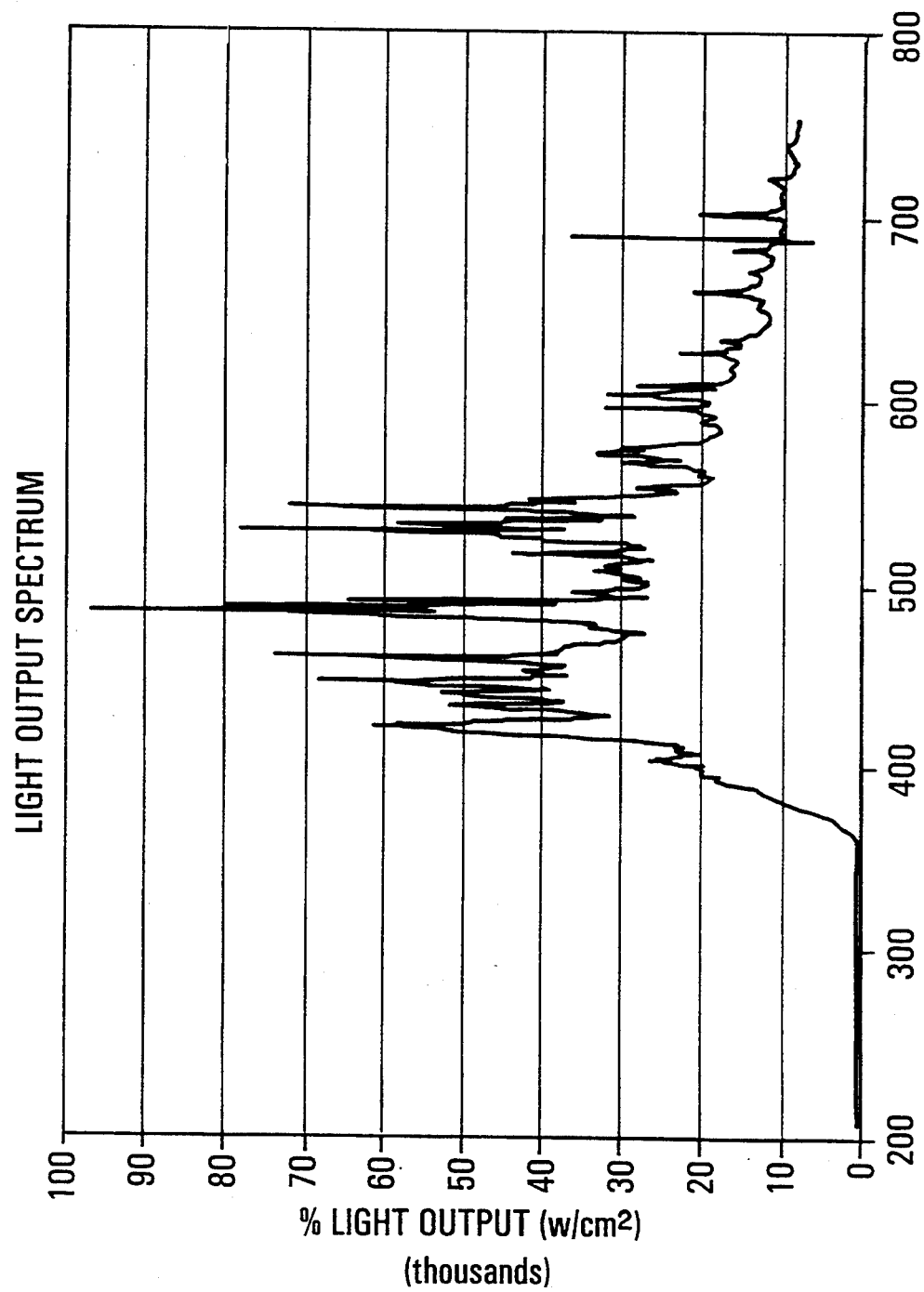
FIG. 2 is a graph showing the light output of a strobe lamp photon source suitable for use in the present invention.

The unfiltered relative spectral radiance of a quartz tungsten halogen lamp useful in the practice of the invention is shown in FIG. 1 of the appended drawings. Alternatively, a strobe lamp can be used to good advantage given that high intensity output is desirable but need not be continuous for the present purposes. The output of a strobe lamp suitable for the present purposes is shown in FIG. 2 of the appended drawings.

Figure 3:
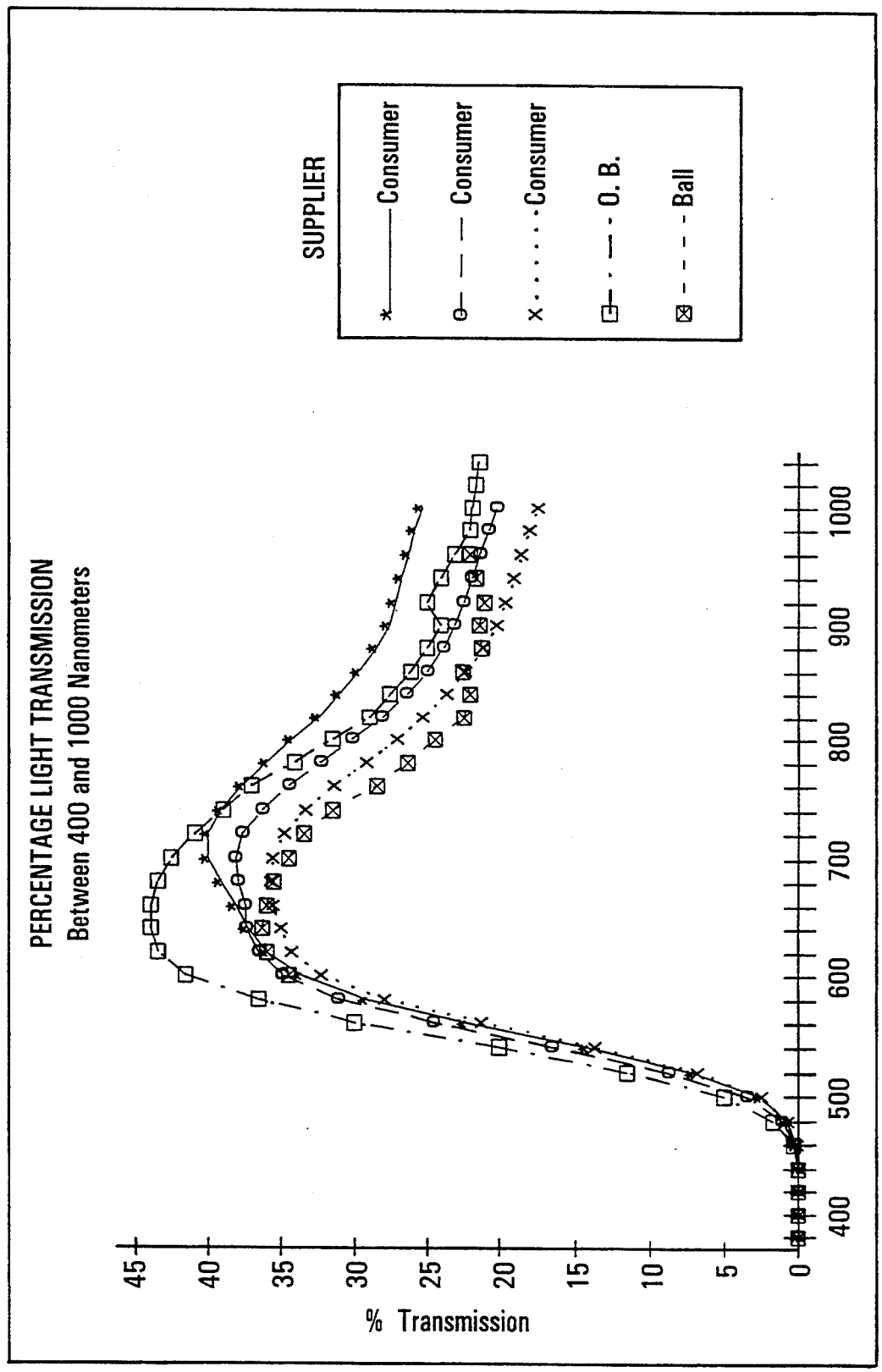
FIG. 3 is a graph illustrating the light transmission spectrum of brown beer bottle glass from various manufacturers.

Filters were selected on the basis of the light transmission properties of typical brown bottle glass compositions commonly employed by the beer industry. A graph illustrating the percentage of light transmitted over a spectrum of wavelengths for such glasses is illustrated in FIG. 3.

In one application, a narrow band optical filter having a peak transmittance at about 480 nm and a 10 nm bandwidth was selected on the basis that the light passed by the filter had essentially zero transmittance in the target glass. Tests showed that this suppressed false-defect signals completely, but at the expense of collaterally suppressing some true-defect signals.

In another application, a narrow-band optical filter having a peak transmittance at about 520 nm, with a 10 nm bandwidth, was selected, on the basis that the light passed from the filter to the glass, would have about 4% transmittance in the glass. In this arrangement, false-defect signals where virtually eliminated, but true-defect signals where actually enhanced compared with the signals using the 480 nm narrow band transmission filter.

Figure 4:
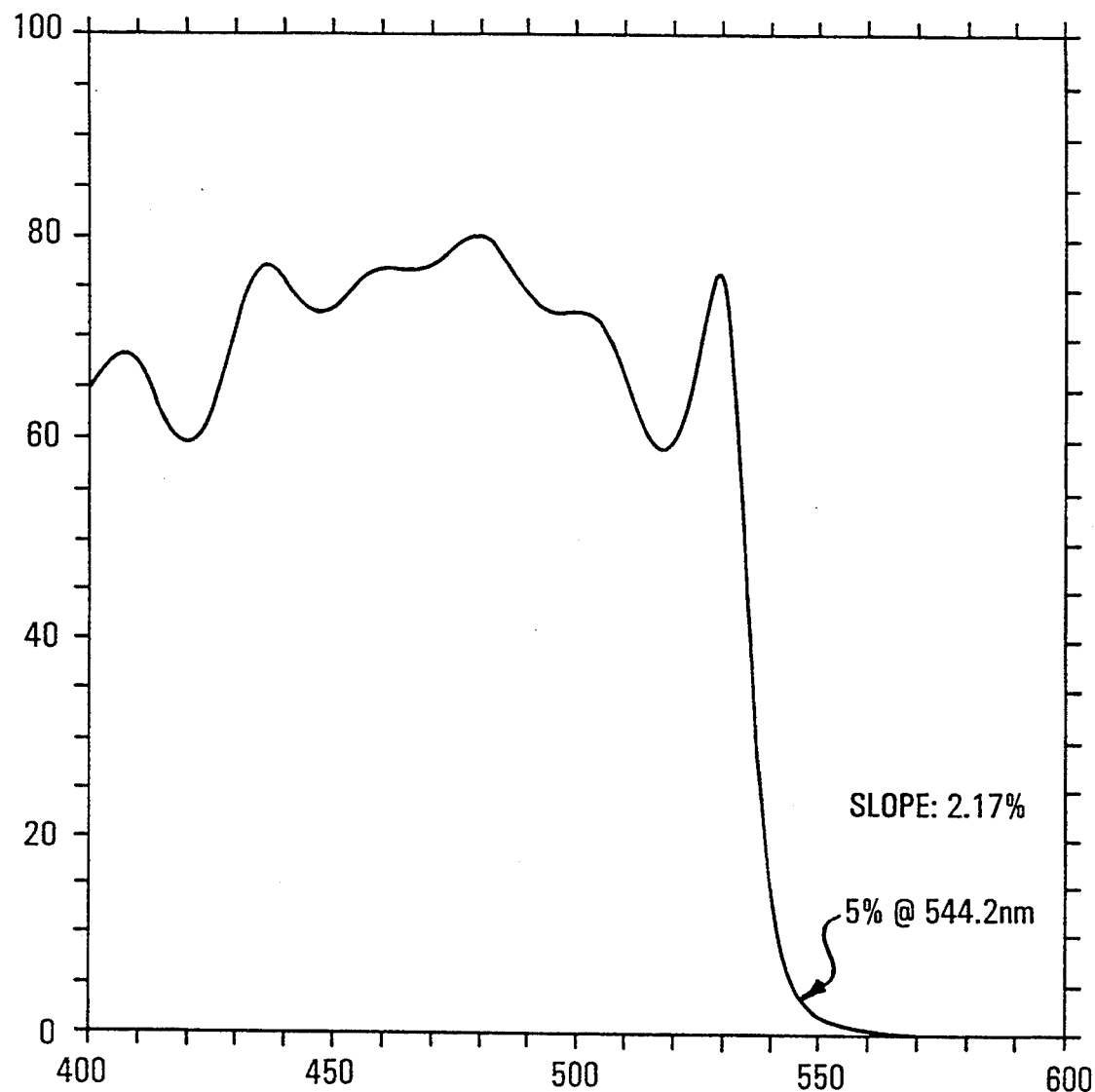
FIG. 4 illustrates the transmissibility characteristics for a 550 nm short pass filter useful in the present invention.
Figure 5A:
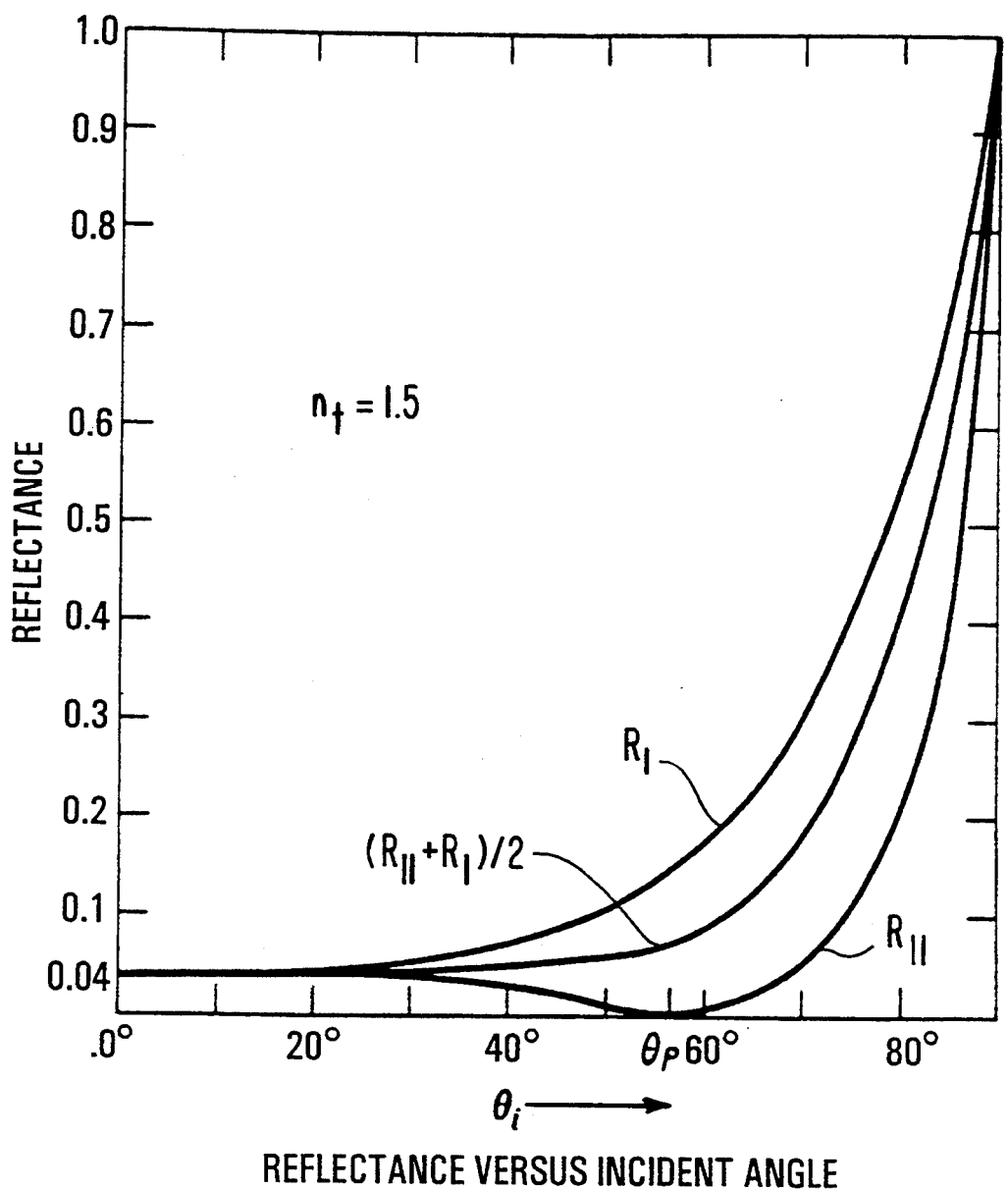
FIG. 5a depicts the reflectance polarization for a reflected polarized incident beam (from a dielectric—ie non-metallic target surface—eg glass), over a range of incident angles.
Figure 5B:
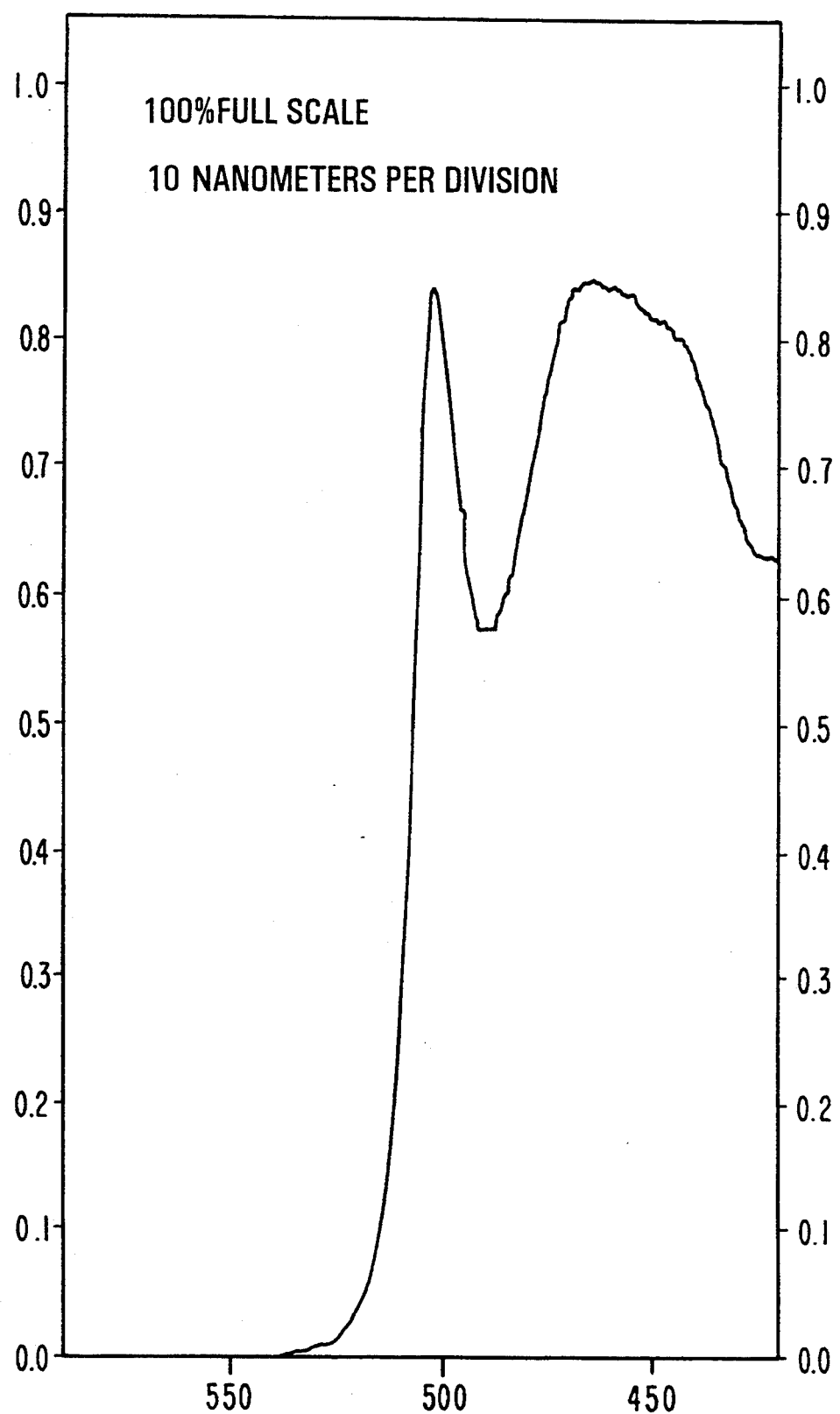
FIG. 5b is a graphical representation of the transmission characteristics of a 500 nanometer short-pass filter useful in the practice of certain aspects of the present invention.
Figure 6A:
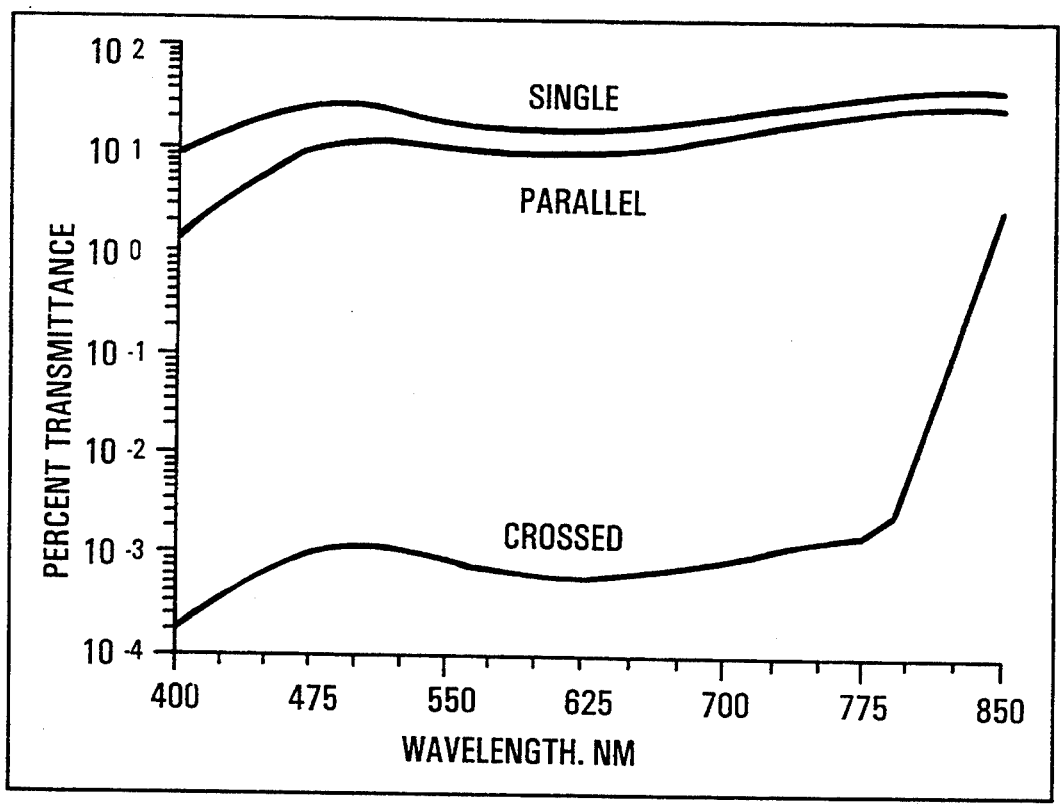
FIG. 6(A–G) is a graphical representation of the transmission characteristics of a cross coupled pair of Polaroid polarizers.
Figure 6B:
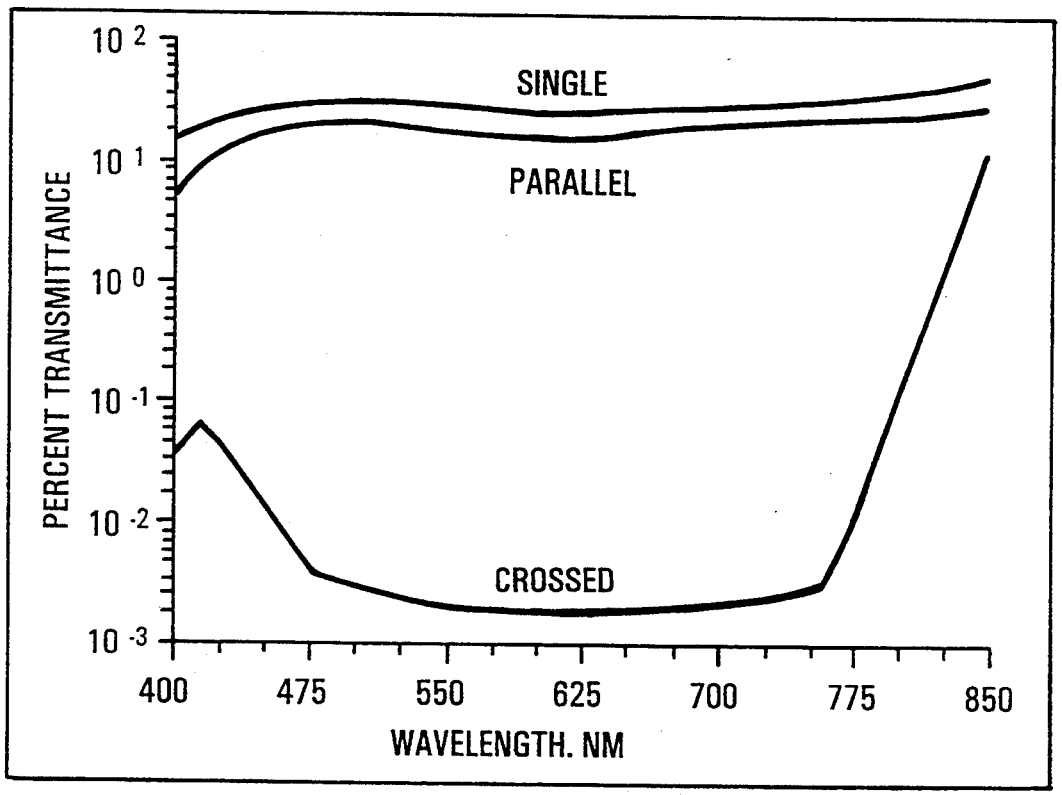
Figure 6C:
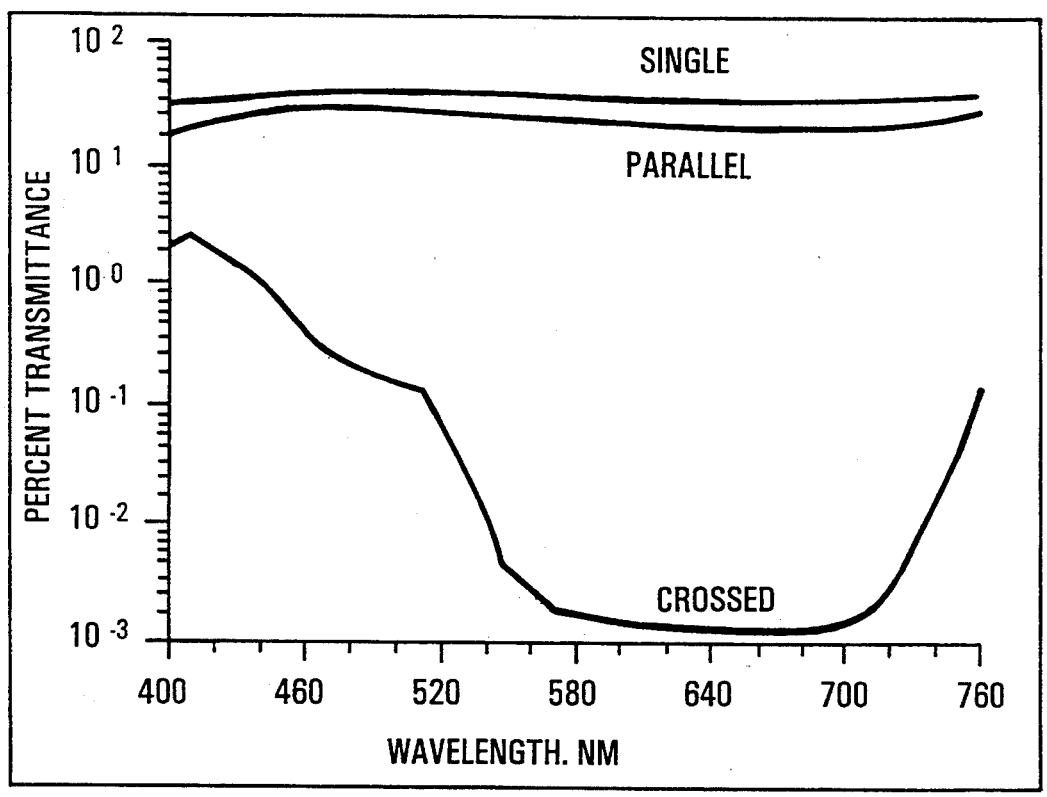
Figure 6D:
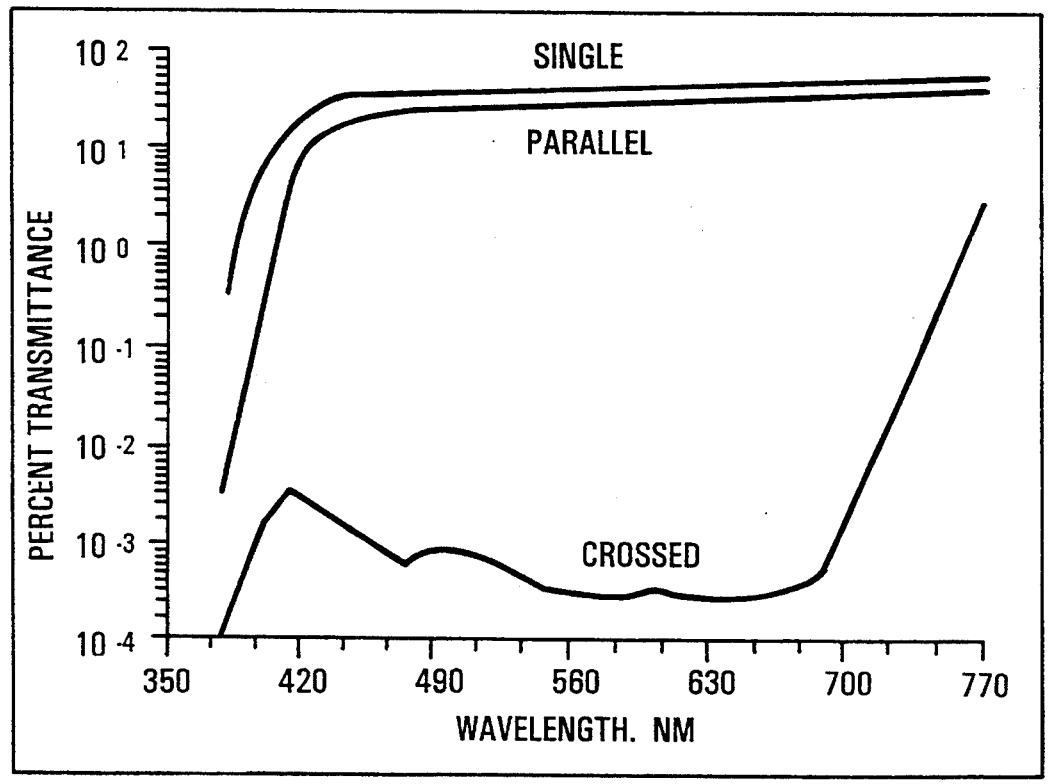
Figure 6E:
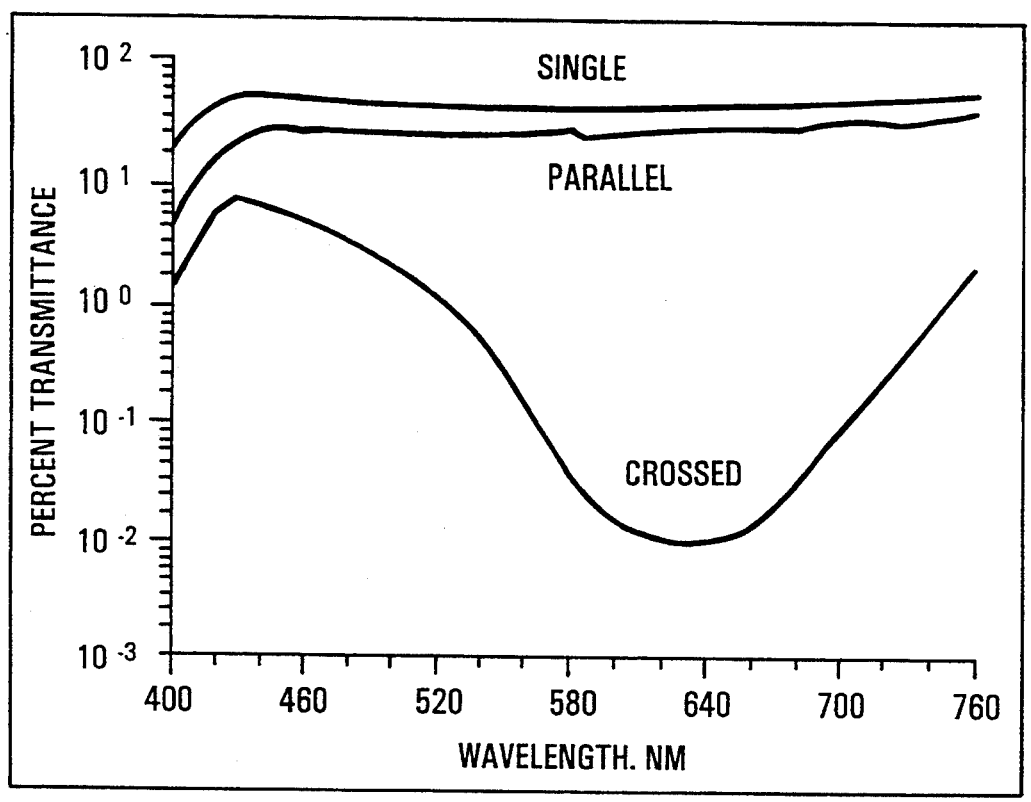
Figure 6F:
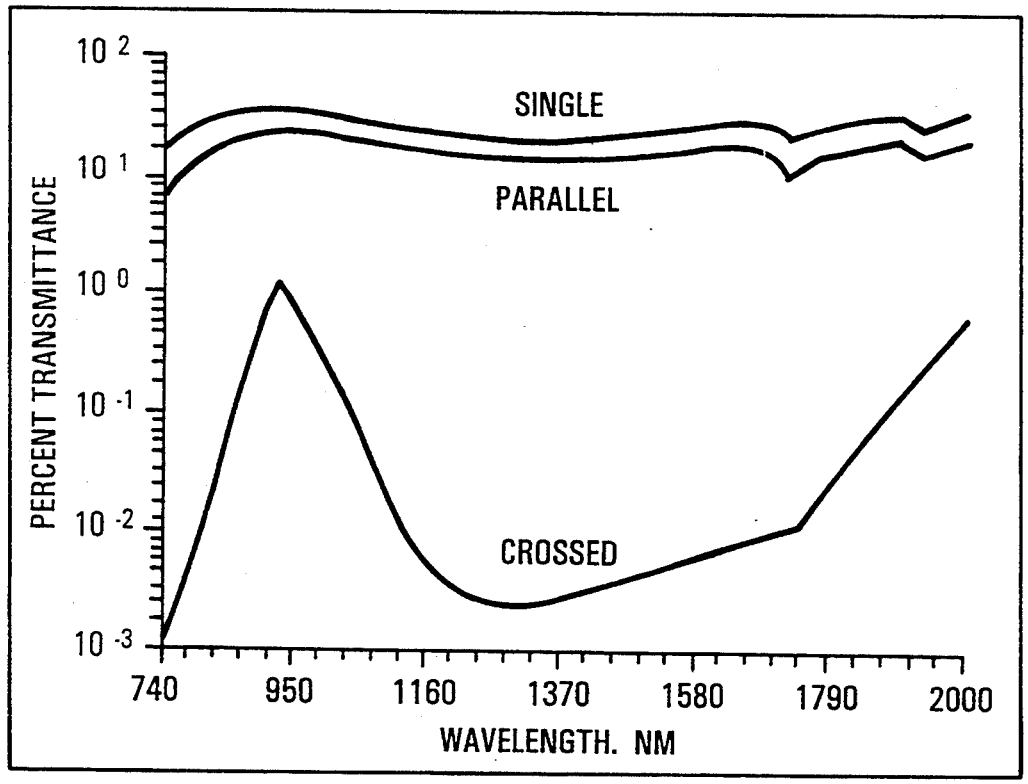
Figure 6G:
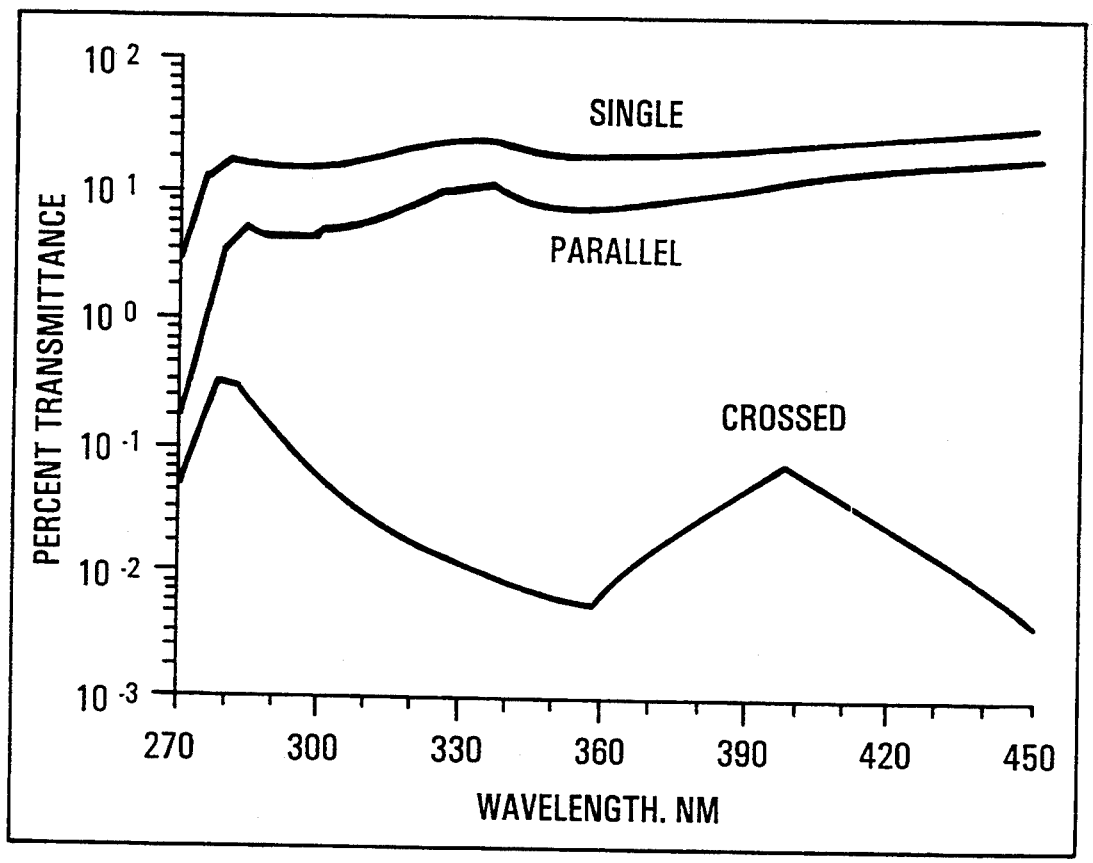

In yet a third application, a short-pass filter was employed with a view to securing the advantages of both of the narrow band filters mentioned in the two preceding paragraphs. The broader spectral transmittance of the short-pass filter combined the benefits of relatively improved suppression of false-defect signals, while at the same time relatively enhancing true-defect signals. Moreover, the greater "amount" of light passed through the short pass filter (that is the broader bandwidth passed a greater amount of incident light on to the target surface), resulted in an overall improvement in intensity, and hence defect detection/discrimination. Two short pass filters were considered for this application—one with a transmission cut-off at about 550 nm, and the other at about 500 nm. Their respective transmission profiles is illustrated in FIGS. 4 and 5. The 550 nm filter is preferred in this particular application.

Note that while the same effects are more difficult to realize through the use of narrow band pass filters in optical "serial" arrangements, an optically "parallel" arrangement of judiciously selected narrow band pass filters could be employed to mimic the broader spectral emissions from a short pass filter, if necessary.

The use of polarizers in the present invention follows from a general observation that defects in the glass target tend to depolarize local surface reflectance. The depolarized reflectance can then be used to distinguish defects from the polarized background reflectance from adjacent "undamaged" surfaces. Polarized incident beams, however, are reflected off of target surfaces in a bi-polarized orientation—one plane being parallel to the incident plane, and the other perpendicular to it. This plurality of reflected planes orientations is undesirable because it blurs the distinction between the background reflectance signal and the depolarized defect signal. Accordingly signal discrimination using a polarized incident beam is carried out by directing the incident beam at the target surface at an angle in the Brewster range, and in particular at the Brewster angle. Over this range, the intensity of reflectance in the perpendicular plane is greater than the intensity of reflectance in the parallel plane. In particular, at the Brewster angle, the intensity of reflectance in the parallel plane is a minimum (essentially zero). This incident angle phenomenon is illustrated in FIG. 5, for glass having a reflectance index of about 1.5. The separation between the amount of light reflected in respective planes of polarizations occurs over a range which as shown, is greater than about 35 degrees to less than 90 degrees, and preferably from greater than 40 to less than 80 degrees. The Brewster angle is about 55 degrees, (with an especially preferred incident range falling between about 50 and 60 degrees).

Figure 7:
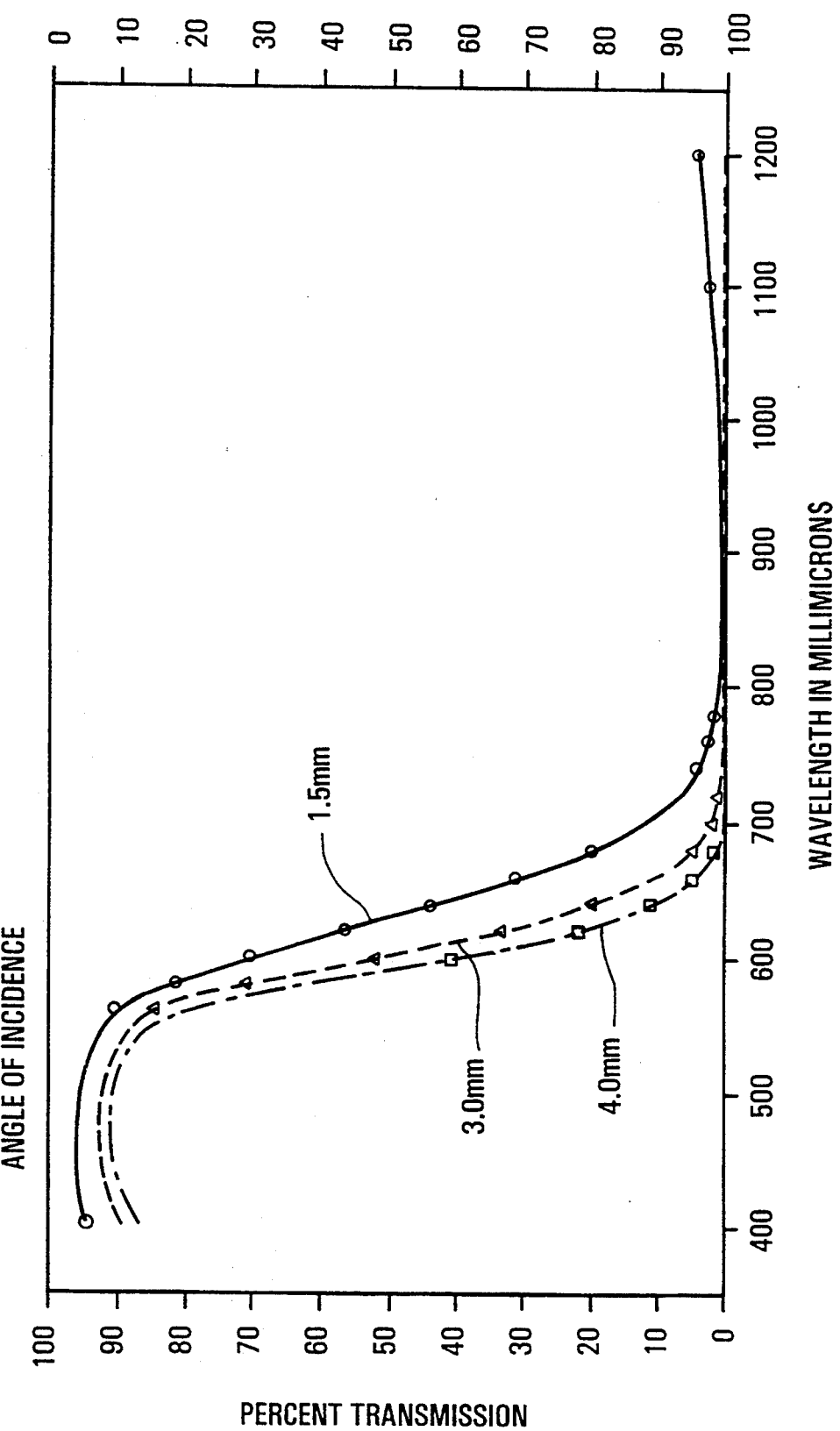
FIG. 7 is also a graphical representation of the transmission profile for an optional low pass filter useful in certain embodiments of the present invention for reducing infrared light present in the light beam.

Polarized detection relies on the use of a crossed polarizer pair of filters comprising a first optical polarizer for polarizing the incident beam into an incident polarized plane, and a second optical polarizer oriented so that its optical rotation is cross polarized in relation to the first polarizer, so that the second discriminates against, (and optimally rejects), reflectance oriented in a plane perpendicular to the incident polarized plane. This darkens the background reflectance and thereby improves the contrast between the background and depolarized defect signals. The crossed polarized rejection rate is illustrated in FIG. 6 for selected Polaroid polarizer sheet materials found useful in the present invention. In the case of the Polaroid materials for which the specifications are given in FIG. 6, the use of an infra red filter—such as an HA11 heat absorbing glass filter having low-reflection coatings on both sides, which is available from Fish-Schurmann Corp) reduces the possible effects of non-polarized infrared light that might otherwise interfere with defect detection. The percentage transmission over a range of wavelengths for this filter is illustrated in FIG. 7. In light of this example, a person skilled in the art will be able to appropriately select filters on an as needed basis.

The silicon photodetector selected for the present practice under the present invention is a CCD silicon photodetector camera, available from RCA. A typical spectral response curve is illustrated in FIG. 8 of the appended drawings. Other detectors which might be used in the practice of the present invention, include Panasonic camera model GP-CD40; Vactec detector model #VTS6079; Hamamatsu detector S639; and, Vactec uv-sensitive detector VTB6060 UV.

In accordance with this preferred practice under the present invention, there is provided an exemplary embodiment as described herein below with particular reference to FIGS. 9, 10 and 11, of the appended drawings, and in accordance with which, there is provided an optical photodetection system for use in glass surface defect photodetection. FIG. 9 depicts the system as a schematic assembly of components including a single, source 1—detector 2 pair, while FIGS. 10 and 11 depict multiple source/detectors in plan and elevated perspective views, respectively. As illustrated, this embodiment relates particularly to a "critical" application of the invention, in which it is employed for screening beer bottle returns, having integrally-formed glass threads along the upper reaches of the bottle neck, for engaging twist-off crowns.

The system includes a source 1 for directing light at wavelengths overlapping a target-glass-absorbed bandwidth, as a plurality of mutually discrete incident beams thereof against a target glass surface 3.

More particularly, the means for directing light comprises a tungsten halogen light source 1 for emitting light. This is optically coupled to a transmission filter 4 selected to transmit incident light at wavelengths substantially overlapping a target-glass-absorbed bandwidth. That filter comprises a short-pass filter selected to pass wavelengths in a transmission bandwidth over a low transmittance range of target glass absorbed wavelengths, (and is fact selected such that the incident light transmitted by this filter has a transmittance in the target glass of about 4%). Also included is a first optical polarizer 5 for polarizing light emitted from said means for directing light, wherein said first optical polarizer 5 is arranged to pass a resultant, filtered, polarized, incident beam 6 against a target glass surface 3.

Detectors 2, comprise video cameras, and are aligned in defect-scattered light beam detecting relation relative to at least one (as shown in FIG. 9), and preferably a plurality (as shown in FIGS. 10 and 11) of incident beams and are thereby operable to generate a detected signal in response to defect-transmitted from said target surface.

Each one of the plurality of detectors comprises at least one silicon photodetector, and further includes a second optical polarizer 7 arranged in cross-polarized relation to said first optical polarizer An infra-red-rejecting filter 8 is operable to screen out wavelengths at which the polarizers are not effective for polarizing such light.

Each of the detectors is aligned at the Brewster angle of 55 degrees relative to the light sources, and is operable to generate a detected signal in response to light transmitted by defects on the target surface.

Each of the detectors comprises a camera including an analog-to-digital detected signal converter operable to provide a digital output signal embodying data representative of said camera's field of view. That data includes a representative array comprising a plurality of reflected-beam-descriptive values for respective ones of a corresponding array of camera-sensed pixels. Each of said values represents a relative intensity of said reflected beam as captured by corresponding ones of pixels. A comparator 9 (which may be a general purpose computer) is employed to establish defect threshold intensity limits and for comparing the values to the limits, in order to identify a defect condition in response to which the comparator generates a defect-condition responsive output signal. In the embodiment illustrated in FIG. 9, this output is passed to a monitor, for visual representation thereof. A simple electronic thresholding circuit may be used. For this same purpose the comparator could alternatively employ a discriminatory paradigm selected, for example, from an electronic threshold filter, a deterministic arithmetic thresholding processor, an expert data base coupled with an inferential engine processor, an auto-associative neural network processor; or, any combination of thereof. These paradigms are utilized to facilitate pattern comparisons between the limits to the values, and on the basis of that comparison, trigger the comparator to generate that defect-condition responsive output signal.

This system further includes bottle conveyance means 11 for delivering glassware to an optical photodetection station adapted for presentation of target surfaces of said glassware in photodetecting register with the system, as well as means for the physical rejection of damaged bottles.

I claim:

1. An optical detection apparatus for use in glass surface defect photodetection, comprising:
   a source for emitting light;
   an optical transmission filter selected to transmit incident light at wavelengths substantially overlapping a target-glass-absorbed bandwidth, and arranged to pass a resultant, incident beam against a first optical polarizer, said first optical polarizer being used to polarize light emitted from said optical transmission filter and arranged to pass a resultant polarized incident beam against a target glass surface;
   a detector comprising:
      an at least one photodetector; and,
      a second optical polarizer arranged in cross-polarized relation to said first optical polarizer;
   said detector being aligned in defect-scattered light beam detecting relation at an angle in the Brewster range, and being operable to generate a detected signal in response to light scattered from defects in said target surface.

2. The apparatus according to claim 1, wherein said detector comprises a camera linked in tandem to an analog-to-digital detected signal converter operable to provide a digital output signal embodying data representative of a camera's field of view.

3. The apparatus according to claim 2, wherein said data includes a representative array comprising a plurality of detected-beam-descriptive values from signal values corresponding to an array of camera-sensed pixels.

4. The apparatus according to claim 3 wherein each of said detected-beam descriptive values represents a relative intensity of said signal values.

5. The apparatus according to claim 4, in combination with a comparator means for establishing defect threshold intensity limits and for comparing said detected-beam-descriptive values to said limits to identify a defect condition, whereupon said comparator generates a defect-condition responsive output signal.

6. The apparatus according to claim 5 wherein the comparator employs a discriminatory paradigm selected from the group consisting of:
an electronic threshold filter;
a deterministic arithmetic thresholding processor;
an expert data base coupled with an inferential engine processor;
an auto-associative neural network processor; or,
any combination of thereof, for comparing said limits to said values and triggering said comparator to generate said defect-condition responsive output signal.

7. The apparatus according to claim 1, wherein said detector further includes a filter operable to filter out light at wavelengths outside of said polarizer's ability to polarize light from said source.

8. The apparatus according to claim 1, wherein said detector is aligned in defect-scattered light beam detecting relation relative to said incident beam at about the Brewster angle.

9. An optical detection apparatus for use in glass surface defect photodetection, comprising:
a source for emitting light;
an optical transmission filter selected to transmit incident light at wavelengths substantially overlapping a target-glass-absorbed bandwidth, and arranged to pass a resultant, incident beam against a target glass surface; and
a detector comprising an at least one photodetector, with said detector being aligned in defect-scattered light beam detecting relation relative to said incident beam and being operable to generate a detected signal in response to light scattered from defects in said target surface.

10. The apparatus according to claim 9 wherein said filter means comprises narrow band pass filter means.

11. The apparatus according to claim 10, wherein said narrow band pass filter means comprises a co-operable pair of narrow band pass filters arranged in optical tandem, and having an overlapping range of transmission bandwidths over a low transmittance range of target glass absorbed wavelengths.

12. The apparatus according to claim 10 wherein said filter is selected such that the incident light transmitted by said filter has a transmittance in said target glass of greater than 0%, and less than 10%.

13. The apparatus according to claim 12, wherein said filter is selected such that the incident light transmitted by said filter has a transmittance in said target glass of less than 5%.

14. The apparatus according to claim 13, wherein said filter is selected such that the incident light transmitted by said filter has a transmittance in said target glass of about 4%.

15. The apparatus according to claim 10, wherein said filter means comprises short-pass filter means selected to pass wavelengths in a transmission bandwidth over a low transmittance range of target glass absorbed wavelengths.

16. An improved optical photodetection apparatus for use in glass surface defect photodetection of the type having:
means for directing light as an incident beam thereof against a target glass surface; and,
a detector aligned in defect-scattered-light detecting relation relative to said incident beam and said surface and being operable to generate a detected signal in response to light scattered from defects in said target surface;
wherein the improvement comprises a increased defect-detecting signal-to-noise ratio in a photodetection apparatus in which:
said means for directing light comprises
a source for emitting light; and
an optical transmission filter selected to transmit incident light at wavelengths substantially overlapping a target-glass-absorbed bandwidth;
said photodetection apparatus further includes a first optical polarizer for polarizing light emitted from said means for directing light, wherein said first optical polarizer is arranged to pass a resultant, polarized, incident beam against a target glass surface;
said detector comprises a photodetector, and further includes a second optical polarizer arranged in cross-polarized relation to said first optical polarizer, and wherein said detector is aligned in defect-scattered light beam detecting relation relative to said incident beam at an angle in the Brewster range, and is operable to generate a detected signal in response to defect scattered light from defects in said target surface.

17. The apparatus according to claim 16, wherein said detector comprises a camera linked in tandem to an analog-to-digital detected signal converter operable to provide a digital output signal embodying data representative of a camera's field of view.

18. The apparatus according to claim 17, wherein said data includes a representative array comprising a plurality of light-beam-descriptive values for a corresponding array of camera-sensed pixels.

19. The apparatus according to claim 18 wherein each of said light-beam-descriptive values represents a relative intensity of said light beam as captured by corresponding ones of pixels.

20. The apparatus according to claim 19, in combination with a comparator means for establishing defect threshold intensity limits and for comparing said light-beam-descriptive values to said limits to identify a defect condition, whereupon said comparator generates a defect-condition responsive output signal.

21. The apparatus according to claim 20 wherein the comparator employs a discriminatory paradigm selected from the group consisting of:
an electronic threshold filter;
a deterministic arithmetic thresholding processor;
an expert data base coupled with an inferential engine processor;
an auto-associative neural network processor; or,
any combination of thereof,
for comparing said limits to said light-beam-descriptive values and triggering said comparator to generate said defect-condition responsive output signal.

22. The apparatus according to claim 17, wherein said detector further includes an optical-matching, infra-red-rejecting filter operable to matchingly-couple said polarizer's effectiveness to said photodetector's sensitivity.

23. The apparatus according to claim 17, wherein said detector is aligned in defect scattered light beam detecting relation relative to said incident beam at about the Brewster angle.

24. The apparatus according to claim 17, wherein said means for directing lights comprises:
   a source for light;
   an optical transmission filter means selected to transmit incident light at wavelengths overlapping a target-glass-absorbed bandwidth, and arranged to pass a resultant, filtered incident beam against a target glass surface.

25. The apparatus according to claim 24 wherein said filter means comprises narrow band pass filter means.

26. The apparatus according to claim 25, wherein said narrow band pass filter means comprises a co-operable pair of narrow band pass filters arranged in optical tandem, and having an overlapping range of transmission bandwidths over a low transmittance range of target glass absorbed wavelengths.

27. The apparatus according to claim 24 wherein said filter is selected such that the incident light transmitted by said filter has a transmittance in said target glass of greater than 0%, and less than 10%.

28. The apparatus according to claim 27, wherein said filter is selected such that the incident light transmitted by said filter has a transmittance in said target glass of less than 5%.

29. The apparatus according to claim 28, wherein said filter is selected such that the incident light transmitted by said filter has a transmittance in said target glass of about 4%.

30. The apparatus according to claim 24, wherein said filter means comprises short-pass filter means selected to pass wavelengths in a transmission bandwidth over a low transmittance range of target glass absorbed wavelengths.

31. An optical photodetection system for use in glass surface defect photodetection including:
   a source for emitting light;
   an optical transmission filter selected to transmit incident light at wavelengths substantially overlapping a target-glass-absorbed bandwidth, and arranged to pass a plurality of mutually discrete incident beams thereof against a target glass surface;
   a first optical polarizer for polarizing light emitted from said optical transmission filter, wherein said first optical polarizer is arranged to pass a resultant, polarized, incident beam against a target glass surface;
   a corresponding plurality of detectors aligned in defect scattered light beam detecting relation relative to respective ones of said incident beams and said surface and being operable to generate a detected signal in response to light scattered through defects in said target surface:
   wherein each one of said plurality of detectors comprises an at least one photodetector, and further includes a second optical polarizer arranged in cross-polarized relation to said first optical polarizer; and,
   wherein each of said detectors is aligned in defect-scattered light beam detecting relation relative to an at least one of said incident beams at an angle in the Brewster range, and is operable to generate a detected signal in response to light scattered through defects in said target surface.

32. The system according to claim 31, wherein said system further includes bottle conveyance means for delivering glassware to an optical photodetection station adapted for presentation of target surfaces of said glassware in photodetecting register with said system.

* * * * *